United States Patent
Nussbaum et al.

(10) Patent No.: US 6,753,451 B2
(45) Date of Patent: Jun. 22, 2004

(54) PROCESS FOR THE PREPARATION OF PHENYLPHENOL COMPOUNDS

(75) Inventors: Klaus Nussbaum, Wehr (DE); Martina Hoffmann, Hausen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/362,480

(22) PCT Filed: Aug. 21, 2001

(86) PCT No.: PCT/EP01/09666

§ 371 (c)(1),
(2), (4) Date: Feb. 25, 2003

(87) PCT Pub. No.: WO02/18311

PCT Pub. Date: Mar. 7, 2002

(65) Prior Publication Data

US 2003/0191349 A1 Oct. 9, 2003

(30) Foreign Application Priority Data

Aug. 28, 2000 (EP) ............................................ 00810767

(51) Int. Cl.⁷ .............................................. C07C 39/12
(52) U.S. Cl. ..................................................... 568/747
(58) Field of Search .......................... 568/747; 768/747

(56) References Cited

U.S. PATENT DOCUMENTS

| 2,247,403 | A | * | 7/1941 | Perkins |
| 2,248,401 | A | * | 7/1941 | Britton |
| 5,723,500 | A | * | 3/1998 | Stringer |
| 6,403,652 | B1 | * | 6/2002 | Brahms et al. |
| 2002/0119106 | A1 | * | 8/2002 | Harper |

* cited by examiner

*Primary Examiner*—Michael L. Shippen
(74) *Attorney, Agent, or Firm*—Kevin T. Mansfield

(57) ABSTRACT

There is described the preparation of phenylphenol compounds of formula (1) by reaction of a keto compound of formula (3) with dioxolane of formula (4) and with an ammonium compound of formula (5) to from β-aminoketone compound of formula (6) (reaction step (I)), reaction of the compound of formula (6) with a compound of formula (7) to form a compound of formula (2) (reaction step (II)), and subsequent alkylation to form a compound of formula (1) (reaction step (III)) in accordance with scheme (A); wherein $R_1$, $R_2$, $R_3$, $R_6$ and $R_7$ are each independently of the others hydrogen or $C_1$–$C_8$alkyl; $R_4$, $R_5$ and $R_8$ are each independently of the others hydrogen or $C_1$–$C_5$alkyl; ant Hal is a halogen atom. The compounds prepared in accordance with the invention are suitable as antimicrobial active substances.

10 Claims, No Drawings

PROCESS FOR THE PREPARATION OF PHENYLPHENOL COMPOUNDS

The present invention relates to a process for the preparation of phenylphenol compounds and to the use of the latter as antibacterial active substances.

The present process for the preparation of phenylphenol compounds of formula

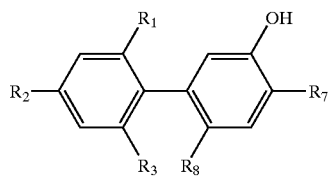
(1)

is carried out in accordance with the invention by reaction of a keto compound of formula

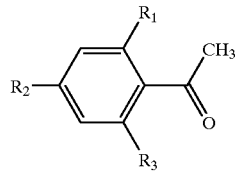
(3)

with dioxolane of formula

(4)

and with an ammonium compound of formula

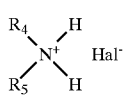
(5)

to form a β-aminoketone compound of formula

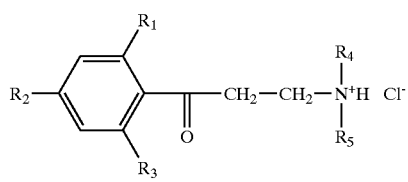
(6)

(reaction step (I)), reaction of the compound of formula (6) with a compound of formula

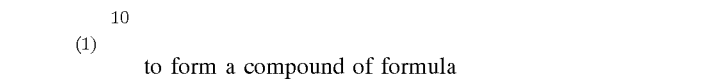
(7)

to form a compound of formula

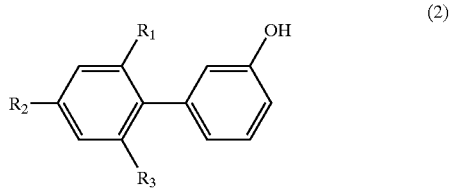
(2)

(reaction step (II)), and subsequent alkylation to form a compound of formula (1) (reaction step (III)) in accordance with the following scheme:

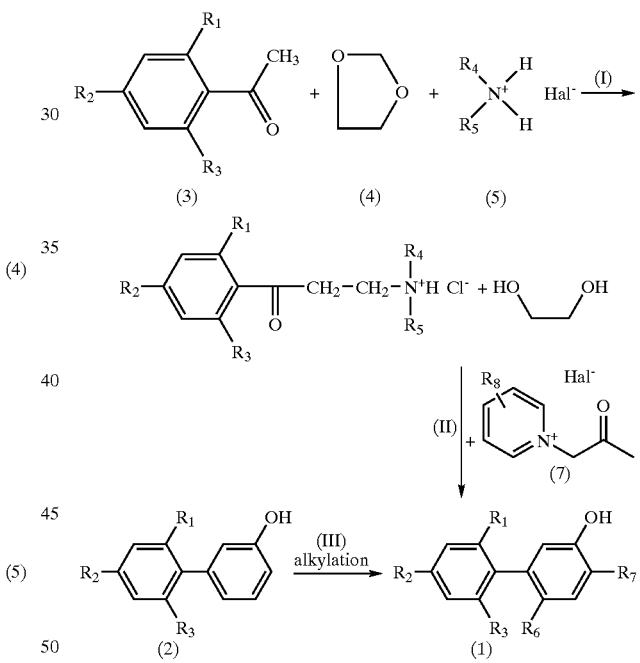

In the above,
  $R_1$, $R_2$, $R_3$, $R_6$ and $R_7$ are each independently of the others hydrogen or $C_1$–$C_8$alkyl;
  $R_4$, $R_5$ and $R_8$ are each independently of the others hydrogen or $C_1$–$C_5$alkyl; and
  Hal is a halogen atom.
  $C_1$–$C_5$Akyl and $C_1$–$C_8$alkyl are straight-chain or branched alkyl radicals, for example methyl, ethyl, propyl, isopropyl, butyl, tert-butyl, pentyl, hexyl, octyl or isooctyl. Some or all of the alkyl radicals may be substituted by $C_3$–$C_6$cycloalkyl, for example cyclopropyl or cyclohexyl, or by $C_1$–$C_7$ side-chain alkyls. Examples of side-chain alkyl radicals include dimethylpropyl, 1,1-dimethyloctyl and tert-butyl-hexyl.

Halogen is fluorine, bromine, iodine or, preferably, chlorine.

The 1,3-dioxolane of formula (4) used as reactant in reaction step (I) can simultaneously also be used as solvent, the amounts used being from 1 to 6 mol, especially from 1 to 5 mol, based on the keto compound of formula (3).

Reaction step (I) is preferably carried out at a temperature of from 60 to 95° C., preferably from 80 to 90° C.

Reaction step (II) is preferably carried out at a temperature of from 60 to 85° C., preferably from 70 to 85° C.

The reaction is preferably carried out in a mixture of ethanol and triethylamine or other suit-able solvents or solvent mixtures.

In formula (2), $R_1$, $R_2$ and $R_3$ are preferably hydrogen. $R_4$ and $R_5$ are preferably methyl or ethyl.

The compound of formula (7) is obtained by the reaction of chloroacetone and pyridine or substituted pyridine:

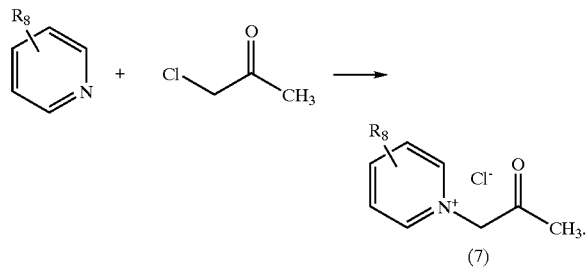

The reaction is preferably carried out in ethanol or other suitable solvents.

For the introduction of $C_1$–$C_8$alkyl radicals $R_1$, $R_2$, $R_3$, $R_6$ and $R_7$, reaction step (III) is preferably a Friedel-Crafts alkylation. The reaction is carried out in the presence of a Lewis acid, e.g. an aluminum halide, especially aluminum chloride, and where appropriate in the presence of a suitable solvent, for example methylene chloride, ethylene chloride, chloroform, $CS_2$ or nitrobenzene. The Lewis acid is used in an amount of from 1 to 3 mol, preferably from 1.25 to 2 mol, based on the compound of formula (2). There comes into consideration as the alkylation reagent for that reaction the corresponding alkyl halide $R_1$-X, $R_2$-X, $R_3$-X, $R_6$-X or $R_7$-X, respectively, X preferably being chlorine. The reaction of the phenol compound of formula (2) with one equivalent of the alkyl halide yields compounds alkyl-substituted ($R_7$) preferentially in the ortho position to the hydroxy group of the compound of formula (1). The reaction of the phenol compound of formula (2) with two or more equivalents of the alkyl halide yields di- or poly-alkylated compounds. Polyalkylation can also be carried out stepwise.

When $R_1$, $R_2$ and $R_3$ in formula (2) are hydrogen, $C_1$–$C_8$alkyl radicals $R_1$, $R_2$ and $R_3$ can preferably be introduced by Friedel-Crafts alkylation.

The present process is concerned more especially with the preparation of compounds of formula (1) wherein
$R_1$, $R_3$ and $R_6$ are hydrogen and
$R_2$ and $R_7$ are $C_1$–$C_8$alkyl,
especially the preparation of the compound of formula

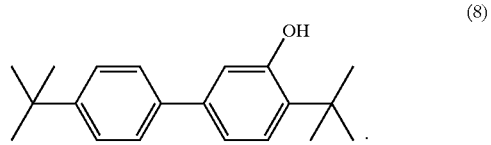

(8)

By way of example, further compounds that can be prepared in accordance with the process of the invention are as follows:

2-tert-butyl-5-phenylphenol
2,4-di-tert-butyl-5-phenylphenol
2-tert-butyl-4-(1,1-dimethylpropyl)-5-phenylphenol
2-tert-butyl-5-(4'-tert-butylphenyl)phenol
2-methyl-5-(4'-cyclopropylphenyl)phenol
2-octyl-5-(4'-cydohexyiphenyl)phenol
2-cyclohexyl-5-(4'-isopropylphenyl)phenol
2,4-diisopropyl-5-phenylphenol
2,4-dicyclopropyl-5-phenylphenol
2,4-dimethyl-5-phenylphenol
2-tert-butyl-5-(4'-isopropylphenyl)phenol
2-tert-butyl-5-(4'-cyclohexylphenyl)phenol
2-tert-butyl-4-(1,1-dimethyloctyl)-5-phenylphenol
2-(1-cyclopropylbutyl)-4-tert-butyl-5-phenylphenol
2-isooctyl-5-phenylphenol
2-cyclopropyl-5-phenylphenol
2-methyl-5-phenylphenol
2-(1-tert-butylhexyl)-5-phenylphenol.

The phenylphenol compounds prepared in accordance with the invention exhibit pronounced antimicrobial action, especially against pathogenic gram-positive and gram-negative bacteria and against bacteria of the skin flora, and also against yeasts and moulds. They are accordingly suitable especially for disinfection, deodorisation, and for general and antimicrobial treatment of the skin and mucosa and of integumentary appendages (hair), more especially for the disinfection of hands and wounds.

They are accordingly suitable as antimicrobial active ingredients and preservatives in personal care preparations, such as shampoos, bath additives, haircare preparations, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders.

The invention accordingly relates also to a personal care preparation comprising at least one compound of formula (1) and cosmetically acceptable carriers or adjuvants.

The personal care preparation according to the invention contains from 0.01 to 15% by weight, preferably from 0.1 to 10% by weight, based on the total weight of the composition, of a compound of formula (1), and cosmetically tolerable adjuvants.

Depending upon the form of the personal care preparation, it comprises, in addition to the phenylphenol compound of formula (1), further constituents, such as sequestering agents, colourings, perfume oils, thickening or solidifying agents (consistency regulators), emollients, UV-absorbers, skin protective agents, antioxidants, additives that improve the mechanical properties, such as dicarboxylic acids and/or aluminium, zinc, calcium or magnesium salts of $C_{14}$–$C_{22}$fatty acids, and, optionally, preservatives.

The personal care preparation according to the invention may be in the form of a water-in-oil or oil-in-water emulsion, an alcoholic or alcohol-containing formulation, a vesicular dispersion of an ionic or non-ionic amphiphilic lipid, a gel, a solid stick or an aerosol formulation.

As a water-in-oil or oil-in-water emulsion the cosmetically tolerable adjuvant contains preferably from 5 to 50% of an oil phase, from 5 to 20% of an emulsifier and from 30 to 90% water. The oil phase may comprise any oil suitable for cosmetic formulations, for example one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention are used in various fields. There come into consideration, for example, especially the following preparations:

- skin-care preparations, e.g. skin-washing and cleansing preparations in the form of tab let-form or liquid soaps, soapless detergents or washing pastes,
- bath preparations, e.g. liquid (foam baths, milks, shower preparations) or solid bath preparations, e.g. bath cubes and bath salts;
- skin-care preparations, e.g. skin emulsions, multi-emulsions or skin oils;
- cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nailcare preparations, such as nail varnish, nail varnish removers, nail hardeners or cuticle removers;
- intimate hygiene preparations, e.g. intimate washing lotions or intimate sprays;
- foot-care preparations, e.g. foot baths, foot powders, foot creams or foot balsams, special deodorants and antiperspirants or callus-removing preparations;
- light-protective preparations, such as sun milks, lotions, creams or oils, sun-blocks or tropicals, pre-tanning preparations or after-sun preparations;
- skin-tanning preparations, e.g. self-tanning creams;
- depigmenting preparations, e.g. preparations for bleaching the skin or skin-lightening preparations;
- insect-repellents, e.g. insect-repellent oils, lotions, sprays or sticks;
- deodorants, such as deodorant sprays, pump-action sprays, deodorant gets, sticks or roll-ons;
- antiperspirants, e.g. antiperspirant sticks, creams or roll-ons;
- preparations for cleansing and caring for blemished skin, e.g. soapless detergents (solid or liquid), peeling or scrub preparations or peeling masks;
- hair-removal preparations In chemical form (depilation), e.g. hair-removing powders, liquid hair-removing preparations, cream- or paste-form hair-removing preparations, hair-removing preparations in gel form or aerosol foams;
- shaving preparations, e.g. shaving soap, foaming shaving creams, non-foaming shaving creams, foams and gels, preshave preparations for dry shaving, after-shaves or after-shave lotions;
- fragrance preparations, e.g. fragrances (eau de Cologne, eau de toilette, eau de parfum, parfum de toilette, perfume), perfume oils or perfume creams;
- dental care, denture-care and mouth-care preparations, e.g. toothpastes, gel toothpastes, tooth powders, mouthwash concentrates, anti-plaque mouthwashes, denture cleaners or denture fixatives;
- cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semipermanent or permanent hair colorants, preparations containing self-oxidising dyes, or natural hair colourants, such as henna or camomile.

An antimicrobial soap has, for example, the following composition:

0.01 to 5% by weight of a compound of formula (1)
0.3 to 1% by weight titanium dioxide,
1 to 10% by weight stearic acid,
ad 100% soap base, e.g. a sodium salt of tallow fatty acid or coconut fatty acid, or glycerol.

A shampoo has, for example, the following composition:

0.01 to 5% by weight of a compound of formula (1),
12.0% by weight sodium laureth-2-sulfate,
4.0% by weight cocamidopropyl betaine,
3.0% by weight NaCl and
water ad 100%.

A deodorant has, for example, the following composition:

0.01 to 5% by weight of a compound of formula (1),
60% by weight ethanol,
0.3% by weight perfume oil, and
water ad 100%.

The invention relates also to an oral composition comprising from 0.01 to 15% by weight based on the total weight of the composition, of a compound of formula (1), and orally tolerable adjuvants.

Example of an oral composition:

10% by weight sorbitol,
10% by weight glycerol,
15% by weight ethanol,
15% by weight propylene glycol,
0.5% by weight sodium lauryl sulfate,
0.25% by weight sodium methylcocyl taurate,
0.25% by weight polyoxypropylene/polyoxyethylene block copolymer,
0.10% by weight peppermint flavouring,
0.1 to 0.5% by weight of a compound of formula (1), and
48.6% by weight water.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The phenylphenol compounds of formula (1) used according to the invention are also suitable for treating, especially preserving, textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton.

The phenylphenol compounds according to the invention are suitable also for treating, especially imparting antimicrobial properties to or preserving, plastics, e.g.

polyethylene, polypropylene, polyurethane, polyester, polyamide, polycarbonate, latex, etc. Fields of use therefor are, for example, floor coverings, plastics coatings, plastics container and packaging materials; kitchen and bathroom utensils (e.g. brushes, shower curtains, sponges, bathmats), latex, filter materials (air and water filters), plastics articles used in the field of medicine, e.g. dressing materials, syringes, catheters etc., so-called "medical devices", gloves and mattresses.

Paper, for example papers used for hygiene purposes, may also be provided with antimicrobial properties using the phenylphenol compounds according to the invention.

It is also possible for nonwovens, e.g. nappies/diapers, sanitary towels, panty liners, and cloths for hygiene and household uses, to be provided with antimicrobial properties in accordance with the invention.

The phenylphenol compounds of formula (1) are also used in washing and cleaning formulations, e.g. in liquid or powder washing agents or softeners.

The phenylphenol compounds of formula (1) can be used especially in household and general-purpose cleaners for cleaning and disinfecting hard surfaces.

A cleaning preparation has, for example, the following composition:

0.01 to 5% of a compound of formula (1)
3.0% octyl alcohol 4EO
1.3% fatty alcohol $C_8$–$C_{10}$polyglucoside
3.0% isopropanol
ad 100% water.

In addition to preserving cosmetic and household products, the preservation of technical products, the provision of technical products with antimicrobial properties and use as a biocide in technical processes are also possible, for example in paper treatment, especially in paper treatment liquors, printing thickeners of starch or of cellulose derivatives, surface coatings and paints.

The phenylphenol compounds of formula (1) are also suitable for the antimicrobial treatment of wood and for the antimicrobial treatment of leather, the preserving of leather and the provision of leather with antimicrobial properties.

The compounds according to the invention are also suitable for the protection of cosmetic products and household products from microbial damage.

The following Examples illustrate the invention.

EXAMPLE 1 a. Preparation of 3-dimethylamino-1-phenylpropan-1-one (Reaction Step (I))

30.0 g of acetophenone are mixed with 24.5 g of dimethylamine hydrochloride and 74.1 g of 1,3-dioxolane, 2.5 g of concentrated hydrochloric acid are added, and the mixture is heated to exactly 90° C. and maintained at that temperature for 3.5 hours. Excess dioxolane is distilled off and the residue is cooled to 0° C. The resulting 3-dimethylamino-1-phenylpropan-1-one of formula

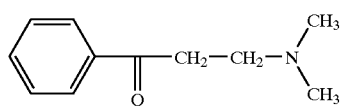

(101a)

crystallises out, is filtered off and subsequently washed with acetone and dried (yield approximately 85% of theory).

Alternatively, after distillation a suspension in ethylene glycol can be further used for the next step.

Instead of distillation, the product can be crystallised out from the reaction mass by cooling to 0° C., filtered off and dried (yield: 91% of theory).

b. Preparation of 3-hydroxybiphenyl (Reaction Step (II))

19.8 g of anhydrous pyridine are added to 100 g of absolute ethanol at room temperature under a dry nitrogen atmosphere, the mixture is heated to 70° C., and 23.1 g of anhydrous chloroacetone are fed in, in the course of which the temperature is able to rise to reflux temperature. The reaction mixture is maintained at that temperature for approximately 1 hour. 72.5 g of triethylamine and also 35.6 g of the compound of formula (101a) are then added and boiling at reflux is carried out for 2 hours. Alternatively, the pyridinium acetonyl chloride obtained in the first stage can be crystallised out by cooling the reaction mass, and filtered off and optionally recrystallised again from ethanol, and dried in vacuo. The acetonylpyridine of formula

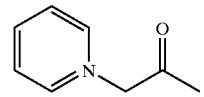

(101b)

so obtained is added to 100 g of ethanol, 72.5 g of triethylamine and 35.6 g of the compound of formula (101a) are added and boiling at reflux is carried out for 2 hours. 3-Hydroxybiphenyl of formula

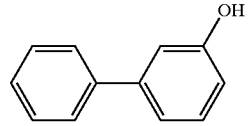

(101c)

is obtained.

Working up can be carried out in a variety of ways:

a. the reaction mass is acidified with HCl and extracted with diethyl ether. The ether extracts are filtered over sodium sulfate and concentrated by evaporation. The product is purified by distillation and/or crystallisation from petroleum ether.

b. the reaction mass is acidified with HCl and extracted with diethyl ether. The ether extracts are extracted repeatedly with approximately 5% sodium hydroxide solution. The combined sodium hydroxide solution extracts are adjusted to a pH value <9 using HCl, an organic phase separating out The organic phase is repeatedly extracted with petroleum ether at elevated temperature and the product is crystallised out from the combined petroleum ether extracts.

c. the pH value is adjusted to >13 using 5% sodium hydroxide solution, the solvent and the amines are distilled off and the reaction mass is extracted with toluene. The extracted reaction mass is adjusted to pH 9 at 80° C and the crude product is separated off from the aqueous phase and recrystallised from petroleum ether.

c. Preparation of 2-tert-butyl-5-(4'-tert-butylphenyl) phenol (Reaction Step (III)):

A mixture of 25 g of the compound of formula (101c) in 100 ml of tert-butyl chloride is stirred and cautiously heated under a nitrogen atmosphere. The mixture is allowed to cool slightly and anhydrous AlCl$_3$ is added. After 1.5 hours, 15 ml of tert-butyl chloride and 0.8 g of AlCl$_3$ are added. The mixture is boiled at reflux for 45 minutes and then 100 ml of chloroform are added. The resulting solution is added to 200 ml of water and mixed well and the organic phase is separated off. The aqueous phase is extracted again with 100 ml of chloroform. The combined organic phases (300 ml) are washed In succession with 100 ml in each case of 6N HCl (2×), water, 5% aqueous sodium hydrogen carbonate solution, water and saturated NaCl soluton. The organic phase is dehydrated over sodium sulfate and concentrated by evaporation in vacuo. The residue is taken up in 150 ml of hexane. The product of formula

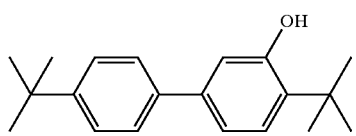

(101)

is crystallised out by cooling, filtered off and dried (yield 29 g, 69.9% of theory).

The crude product recrystallised from hexane again (yield 22.3 g, 53.8% of theory).

What is claimed is:

1. A process for the preparation of a phenylphenol compound of formula

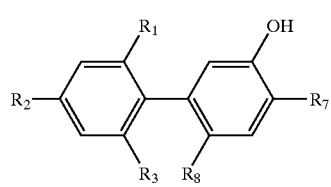

(1)

by reaction of a keto compound of formula

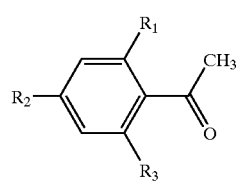

(3)

with dioxolane of formula

(4)

and with an ammonium compound of formula

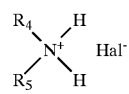

(5)

to yield a β-aminoketone compound of formula

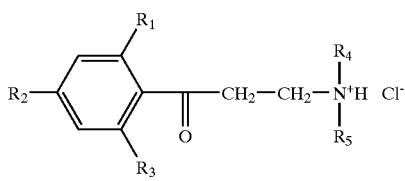

(6)

in reaction step (I), reaction of the compound of formula (6) with a compound of formula

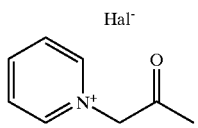

(7)

to form a compound of formula

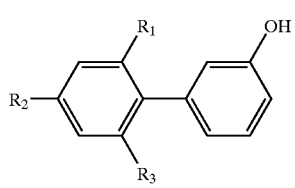

(2)

in reaction step (II), and subsequent alkylation to form a compound of formula (1) in reaction step (III) in accordance with the following scheme:

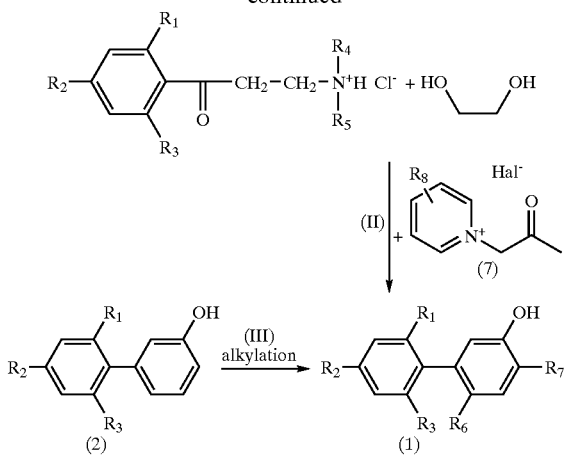

wherein

R$_1$, R$_2$, R$_3$, R$_6$ and R$_7$ are each independently of the others hydrogen or C$_1$–C$_8$alkyl;

R$_4$, R$_5$ and R$_6$ are each independently of the others hydrogen or C$_1$–C$_5$alkyl; and Hal is a halogen atom.

2. A process according to claim 1, wherein the 1,3-dioxolane of formula (4) is also used as solvent.

3. A process according to claim 2, wherein the 1,3-dioxolane is used in a ratio of from 1 to 6 mol based on the keto compound of formula (3).

4. A process according to claim 1, wherein Hal is chlorine.

5. A process according to claim 1, wherein in formula (2) R$_1$, R$_2$ and R$_3$ are hydrogen.

6. A process according claim 1, wherein R$_4$ and R$_5$ are methyl.

7. A process according to claim 1, wherein reaction step (III) is a Friedel-Crafts alkylation.

8. A process according to claim 7, wherein when R$_1$, R$_2$ and R$_3$ in formula (2) are hydrogen, C$_1$–C$_8$alkyl radicals R$_1$, R$_2$ and R$_3$ are introduced by Friedel-Crafts alkylation.

9. A process according to claim 1, which produces a compound of formula (1)

wherein

R$_1$, R$_3$ and R$_6$ are hydrogen and

R$_2$ and R$_7$ are C$_1$–C$_8$alkyl.

10. A process according to claim 9, which produces the compound of formula

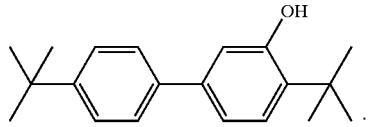

(8)

* * * * *